(12) United States Patent
Watson et al.

(10) Patent No.: US 9,676,685 B2
(45) Date of Patent: Jun. 13, 2017

(54) SELECTIVE HYDROGENATION PROCESS

(71) Applicant: DOW TECHNOLOGY INVESTMENTS LLC, Midland, MI (US)

(72) Inventors: Rick B. Watson, Missouri, TX (US); Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 0 days.

(21) Appl. No.: 14/889,350

(22) PCT Filed: Jun. 19, 2014

(86) PCT No.: PCT/US2014/043114
§ 371 (c)(1),
(2) Date: Nov. 5, 2015

(87) PCT Pub. No.: WO2014/209736
PCT Pub. Date: Dec. 31, 2014

(65) Prior Publication Data
US 2016/0096785 A1    Apr. 7, 2016

Related U.S. Application Data

(60) Provisional application No. 61/839,099, filed on Jun. 25, 2013.

(51) Int. Cl.
*C07C 45/50* (2006.01)
*C07C 7/163* (2006.01)
*C10G 45/32* (2006.01)

(52) U.S. Cl.
CPC .............. *C07C 7/163* (2013.01); *C07C 45/50* (2013.01); *C10G 45/32* (2013.01); *C10G 2300/1092* (2013.01); *C10G 2400/20* (2013.01)

(58) Field of Classification Search
CPC ............. C07C 45/50; C07C 7/163; C07C 5/05
USPC ................................... 568/451; 585/259, 273
See application file for complete search history.

(56) References Cited

U.S. PATENT DOCUMENTS

| | | |
|---|---|---|
| 4,469,907 A | 9/1984 | Araki et al. |
| 4,517,395 A | 5/1985 | Obenaus et al. |
| 4,518,809 A | 5/1985 | Forster et al. |
| 4,528,403 A | 7/1985 | Tano et al. |
| 4,570,025 A | 2/1986 | Nowack et al. |
| 4,705,906 A | 11/1987 | Brophy et al. |
| 4,831,200 A | 5/1989 | Debras et al. |
| 4,906,602 A | 3/1990 | Schneider et al. |
| 5,059,732 A | 10/1991 | Cosyns et al. |
| 5,157,183 A | 10/1992 | Cotterman et al. |
| 5,227,553 A | 7/1993 | Polanek et al. |
| 5,281,753 A | 1/1994 | Olson et al. |
| 5,847,250 A | 12/1998 | Flick et al. |
| 6,350,717 B1 | 2/2002 | Frenzel et al. |
| 6,365,790 B2 | 4/2002 | Reimer et al. |
| 6,437,206 B1 | 8/2002 | Meyer et al. |
| 6,509,292 B1 | 1/2003 | Blankenship et al. |
| 6,734,130 B2 | 5/2004 | Cheung et al. |
| 7,038,096 B2 | 5/2006 | Cheung et al. |
| 7,038,097 B2 | 5/2006 | Molinier et al. |
| 7,045,670 B2 | 5/2006 | Johnson et al. |
| 7,408,091 B2 | 8/2008 | Johnson et al. |
| 7,919,431 B2 | 4/2011 | Johnson et al. |
| 8,013,197 B2 | 9/2011 | Peterson et al. |
| 8,859,834 B2 | 10/2014 | Boeing et al. |
| 2006/0235255 A1 | 10/2006 | Gartside et al. |
| 2010/0006980 A1 | 1/2010 | Yoshinaga |

OTHER PUBLICATIONS

PCT/US2014/043114, International Search Report and Written Opinion with a mailing date of Oct. 22, 2014.
PCT/US2014/043114, International Preliminary Report on Patentability with a mailing date of Dec. 29, 2015.

*Primary Examiner* — Sikarl Witherspoon

(57) ABSTRACT

A process for reducing the diene content of an olefin by feeding hydrogen to the process in stages.

13 Claims, No Drawings

SELECTIVE HYDROGENATION PROCESS

CROSS-REFERENCE TO RELATED APPLICATIONS

This application claims priority from provisional application Ser. No. 61/839,099, filed Jun. 25, 2013, which is incorporated herein by reference in its entirety.

BACKGROUND OF THE INVENTION

The invention relates to a process for purifying a feed stream to a hydroformylation process.

A commonly practiced hydroformylation process reacts an olefin with CO and hydrogen to make an aldehyde. Commercial olefin feedstocks can contain unsaturated impurities such as methylacetylene (propyne) and propadiene, commonly referred to as MAPP gas, and 1,3-butadiene. These impurities can strongly bind to the hydroformylation catalyst as a poison/inhibitor. To remove these impurities, the liquid feedstocks can be sent through clean-up beds (referred to as MAPP beds) designed to react out small levels of polyunsaturated contaminants using a selective hydrogenation catalyst. If the concentration of 1,3-butadiene is too high, conventional MAPP bed operation is insufficient to reduce the concentration below levels that will be detrimental to hydroformylation activity while at the same time protecting the linear (1-butene) present in the feedstock.

It would be desirable to have an improved process for reducing the amount of unsaturated hydrocarbon impurities from hydroformylation feedstocks.

SUMMARY OF THE INVENTION

The process of the invention is such a process comprising: contacting a liquid phase olefin stream containing from 200 ppm to 2 wt. % 1,3-butadiene, based on the total weight of the olefin stream, with a single catalyst and hydrogen in the substantial absence of carbon monoxide, wherein the contacting is conducted: (a) such that the hydrogen is fed into the process at least 2 different hydrogen feed points, and the amount of hydrogen fed to at least one feed point is a substoichiometric amount, relative to the amount of the butadiene, and (b) under hydrogenation conditions sufficient to reduce the concentration of 1,3-butadiene to less than 100 ppm in at least one effluent stream of the process.

Surprisingly, the removal of low levels of 1,3-butadiene from a multi-component $C_4$ hydrocarbon stream by a staged addition of hydrogen, rather than introducing the same amount of hydrogen via a single inlet at the beginning of the reaction, reduces the 1,3-butadiene to lower levels while preserving more 1-butene.

DETAILED DESCRIPTION OF THE INVENTION

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.). For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

Also herein, the recitations of numerical ranges and/or numerical values, including such recitations in the claims, can be read to include the term "about." In such instances the term "about" refers to numerical ranges and/or numerical values that are substantially the same as those recited herein.

Unless stated to the contrary, or implicit from the context, all parts and percentages are based on weight and all test methods are current as of the filing date of this application. For purposes of United States patent practice, the contents of any referenced patent, patent application or publication are incorporated by reference in their entirety (or its equivalent U.S. version is so incorporated by reference) especially with respect to the disclosure of definitions (to the extent not inconsistent with any definitions specifically provided in this disclosure) and general knowledge in the art.

As used herein, the term "ppm" means part per million by weight.

For purposes of this invention, the term "hydrocarbon" is contemplated to include all permissible compounds having at least one hydrogen and one carbon atom. Such permissible compounds may also have one or more heteroatoms. In a broad aspect, the permissible hydrocarbons include acyclic (with or without heteroatoms) and cyclic, branched and unbranched, carbocyclic and heterocyclic, aromatic and nonaromatic organic compounds that can be substituted or unsubstituted.

As used herein, the term "substituted" is contemplated to include all permissible substituents of organic compounds unless otherwise indicated. In a broad aspect, the permissible substituents include acyclic and cyclic, branched and unbranched, carbocyclic and heterocyclic, aromatic and nonaromatic substituents of organic compounds. Illustrative substituents include, for example, alkyl, alkyloxy, aryl, aryloxy, hydroxyalkyl, aminoalkyl, in which the number of carbons can range from 1 to 20 or more, preferably from 1 to 12, as well as hydroxy, halo, and amino. The permissible substituents can be one or more and the same or different for appropriate organic compounds. This invention is not intended to be limited in any manner by the permissible substituents of organic compounds.

As used herein, the term "hydroformylation" is contemplated to include, but not limited to, all permissible asymmetric and non-asymmetric hydroformylation processes that involve converting one or more substituted or unsubstituted olefinic compounds or a reaction mixture comprising one or more substituted or unsubstituted olefinic compounds to one or more substituted or unsubstituted aldehydes or a reaction mixture comprising one or more substituted or unsubstituted aldehydes.

For purposes of this invention, the conversion of butadiene is determined using gas chromatography (GC), based on the concentration of butadiene in the feed to the process.

All references to the Periodic Table of the Elements and the various groups therein are to the version published in the CRC Handbook of Chemistry and Physics, 72nd Ed. (1991-1992) CRC Press, at page 1-10.

"Downstream" means that an element of a process is located or performed after that of a reference process element, e.g., the extraction zone of the hydroformylation process is located after or downstream of the separation zone, which is located after or downstream of the reaction zone.

The process of the invention employs an olefin, hydrogen and a catalyst.

Hydrogen may be obtained from any suitable source, including petroleum cracking and refinery operations. The hydrogen may contain small amounts of other gases. In one embodiment of the invention, the total amount of hydrogen employed is at least an amount sufficient to hydrogenate the entire amount of diene(s) the present in the olefin.

The catalyst can be any catalyst suitable for the selective hydrogenation of butadiene. Many hydrogenation catalysts are known to those skilled in the art, and many are commercially available. Examples of suitable catalysts include supported noble metal catalysts comprising platinum, silver, gold, palladium, rhodium, ruthenium, and osmium. Mixed metal catalysts can be employed. Examples of suitable supports include the oxides of aluminum, silicon and titanium with or without other metal oxide additives or activated carbon. An example of a preferred catalyst is palladium supported on alumina. The catalyst is employed in a catalytic amount. In one embodiment of the invention, the amount of catalyst is sufficient to process the required throughput of hydrocarbons. In one embodiment of the invention, only a single catalyst is employed. For the purposes of the invention, the term "single catalyst" includes not only a catalyst of a uniform composition, but also a catalyst that, when loaded into a reaction zone, has an essentially uniform composition, which composition changes, either uniformly or nonuniformly throughout the catalyst bed, during the lifetime of catalyst.

The olefin can be substituted or unsubstituted, and includes both optically active (prochiral and chiral) and non-optically active (achiral) olefinic unsaturated compounds containing from 2 to 40, preferably 3 to 20, carbon atoms. These compounds are described in detail in US 2010/006980. Such olefinic unsaturated compounds can be terminally or internally unsaturated and be of straight-chain, branched chain or cyclic structures, as well as olefin mixtures, such as obtained from the oligomerization of propene, butene, isobutene, etc. (such as so called dimeric, trimeric or tetrameric propylene and the like, as disclosed, for example, in U.S. Pat. Nos. 4,518,809 and 4,528,403). Unsubstituted olefins are preferred. Preferred olefins are monoethylenically unsaturated and include, for example, propylene, and mixtures of butenes, e.g., mixtures of 1-butene and 2-butene.

As mentioned hereinabove, the olefin feed stream can contain various polyunsaturated hydrocarbon impurities that are detrimental to the hydroformylation reaction. Butadiene is especially detrimental. In one embodiment of the invention, the 1,3-butadiene content of the olefin fed to the process of the invention is from 200 ppm to 2 wt. % 1,3-butadiene based on the total weight of the olefin feed stream. In one embodiment of the invention, the olefin stream comprises primarily butenes, such as from more than 50 up to 95 weight percent butenes. The olefin may also contain dissolved inert gases, such as propane, and butanes. The olefin may contain other impurities, as known by those skilled in the art.

In one embodiment of the invention, the process of the invention is a process for hydrogenating a diolefin, the process comprising: contacting a liquid phase olefin comprising 200 ppm to 2 wt. % 1,3-butadiene, based on the total weight of the olefin feed stream, including impurities, with a single catalyst and hydrogen in the substantial absence of carbon monoxide, wherein the contacting is conducted: (a) such that the hydrogen is fed into the process at least 2 different hydrogen feed points, and (b) under hydrogenation conditions sufficient to reduce the concentration of 1,3-butadiene to less than 50 ppm in at least one effluent stream of the process. The amount of hydrogen, at least at one feed point, such as the first hydrogen feed point, is a substoichiometric amount relative to the amount of the butadiene.

In one embodiment of the invention, the hydrogen feed points are at different locations along the length of the reaction zone. For example, the first hydrogen feed point can be at the front end of a first reaction zone, while at least one subsequent hydrogen feed point can be downstream from the first hydrogen feed point, such as at a point in the reaction zone at which the initial hydrogen feed has been substantially depleted, e.g., via participation in the hydrogenation reaction. In another example, a process can be configured such that a first reaction zone is in a first reactor and a second reaction zone can be in a second reactor, etc. In one embodiment, a single reactor may contain multiple reaction zones and may have multiple hydrogen feed points along its length.

For the purposes of the invention, the term "different hydrogen feed points" means that the hydrogen is fed at feed points at different locations along the length of the process, as measured by conversion of 1,3-butadiene. In one embodiment of the invention, at a first feed point, the conversion of 1,3-butadiene is essentially zero, while at least one subsequent feed point the conversion of 1,3-butadiene is greater than zero, e.g., at least 20%, at least 30%, at least 40%, at least 50%, at least 60%, at least 70%, or higher. The number of feed points is not particularly limited, although in practice the cost of additional feed points will be balanced against additional, incremental process results.

In one embodiment of the invention, multiple reaction zones are employed, and hydrogen is distributed to more than one of the reaction zones to maximize the selectivity of the hydrogenation toward 1,3-butadiene removal in each reaction zone. When the hydrogen is completely converted in the first reaction zone, hydrogen is added to as many additional feed points as are required to achieve removal of the 1,3-butadiene to below 50 ppm while maximizing desired selectivity.

The total amount of hydrogen advantageously is not added to a single input point. Thus, the amount of hydrogen fed to any given process feed point is less than the stoichiometric amount required to hydrogenate the entire amount of diene(s) present in the initial olefin feed stream.

The hydrogenation may be conducted under any set of conditions that results in the desired reduction in 1,3-butadiene content. In various embodiments of the invention, the hydrogenation temperature is from 0 to 120° C., or from 20 to 50° C., and the pressure is from 4 to 14 bar, or from 8 to 12 bar. In one embodiment of the invention, the liquid hourly space velocity (LHSV) is from 0.5 to 50 $hr^{-1}$. The olefin advantageously is fed in the liquid phase.

The process of the invention reduces 1-butene loss from unselective hydrogenation to n-butane by requiring less hydrogen to achieve the same or greater level of 1,3-butadiene removal. Because less hydrogen is required to achieve the removal, excess temperatures caused by over-hydrogenation of the 1-butene to n-butane are not generated, thus minimizing isomerization loses of 1-butene to cis and trans 2-butenes.

In various embodiments, the process of the invention produces a product stream having a 1,3-butadiene content of less than 100 ppm, or less than 50 ppm, or less than 47 ppm. For example, the product stream may contain from zero up to less than 100 ppm, or from zero to 50 ppm, 1,3-butadiene. In one embodiment of the invention, the amount of 1,3-butadiene is from 5 to 50 ppm in the hydrogenation reactor effluent stream.

Specific Embodiments of the Invention

The following examples are given to illustrate the invention and should not be construed as limiting its scope.

General Procedure

For all examples, a mixed $C_4$ hydrocarbon stream is passed, as a liquid, through tubes packed with pretreated 0.1 wt % palladium on alpha-alumina (Sud Chemie G68-E) catalyst in 1/16" extrudate form. Prior to testing, the catalysts are pre-treated. Each bed is heated under pure nitrogen flow to 120° C. to remove any moisture. Hydrogen flow is increased as nitrogen is decreased in a step-wise fashion over 15 minutes until pure hydrogen is flowing at the manufacturer's-recommended rate of 200 cc $H_2$/hr/cc catalyst. The catalysts are soaked under pure hydrogen at 120° C. for 5 hours followed by a cool-down under nitrogen. Each packed tube is installed with a tee for gaseous hydrogen introduction via mass flow meters thus creating "reaction zones." Liquid $C_4$ hydrocarbons are only introduced at the beginning of the first reaction zone. Each reaction zone contains a 3 inch mixing zone at the inlet at the bottom of the zone containing quartz wool/glass beads, and a 1 inch quartz wool packing on top of the catalyst. The pressure of the beds is controlled with back pressure regulators and is 200 psig (1.38 MPa). Sampling of pre- and post-reaction zone bed $C_4$ streams is performed via septum sampling using a 0-100 μL VICI gas tight syringe. The samples are analyzed by GC. Area percent normalization up to the $C_5$ components is used as the main quantification method. Two separate feedstocks of $C_4$ liquids are used. For Comparative Experiment 1 and Comparative Experiment 2, the feed composition is given in Table 1. For Example 3 and Comparative Experiment 4 the feedstock composition is given in Table 4.

TABLE 1

Mixed $C_4$ hydrocarbon feed stream composition for and Comparative Experiments 1 and 2.

| | Wt % |
|---|---|
| Propane | 0.158 |
| Cyclopropane | 0.032 |
| Propylene | 0.091 |
| Isobutane | 0.478 |
| Butane | 4.22 |
| Cyclic C4 | 0.024 |
| trans-2-Butene | 31.8 |
| 1-Butene | 32.3 |
| Isobutene | 6.19 |
| cis-2-Butene | 22.5 |
| Isopentane | 0.041 |
| 1,3-Butadiene | 1.88 |
| Isopentene | 0.148 |
| Pentane Isomer-1 | 0.036 |
| Pentane Isomer-2 | 0.033 |

COMPARATIVE EXPERIMENT 1

Not an Embodiment of the Invention

The General Procedure is followed except as noted. Two reaction zones in series are created consisting of ½" stainless steel tubes, zone 1 with 30.0 g catalyst and zone 2 with 11.3 g catalyst. No external heating or cooling is applied to the reaction zones. The total $C_4$ hydrocarbon flow is 15 mL/hr, providing an overall liquid hourly space velocity (LHSV) of 1.4 $hr^{-1}$ (mL $C_4$ flow per hour divided by catalyst volume). Each reaction zone is fed with a 0.60 mL/min gaseous hydrogen flow thus providing a hydrogen to 1,3-butadiene molar ratio as shown in Table 2. Analysis of the outlet of reaction zone 1 is not performed in this example.

TABLE 2

Results of C.E. 1; 1,3-butadiene (BD) removal from $C_4$ hydrocarbons using staged hydrogen addition.

| | 1-butene wt % | % 1-Butene loss | n-butane wt % | Cis + trans 2-butene wt % | 1,3 butadiene ppm | LHSV (hr−1) | Calculated wt % $H_2$ at bed inlet | $H_2$/BD molar in bed at inlet |
|---|---|---|---|---|---|---|---|---|
| Feed | 32.25 | | 4.22 | 54.31 | 18752 | 1.4 overall | 0.122 overall | 3.5 overall |
| Zone 1 outlet | Not measured | Not measured | Not measured | Not measured | Not measured | 2 | 0.061 | 1.8 |
| Zone 2 outlet | 19.28 | 40.21 | 8.133 | 64.90 | 876 | 4.8 | 0.061 | Not measured |

The "overall" LHSV is calculated by the ratio of the flowrate of the hydrocarbon stream by the total volume (zone 1+zone 2) of the catalyst whereas the LHSV for each reaction zone is calculated by the total hydrocarbon flow divided by the catalyst volume for that particular zone. The "overall" $H_2$/BD ratio is calculated as the total amount of hydrogen added (zone 1+zone 2) to the BD amount entering zone 1. The $H_2$/BD ratio in zone 1 is calculated as the ratio of hydrogen introduced to just zone 1 divided by the BD content entering zone 1. The amount of BD exiting zone 1 is not measured in this example.

The butadiene concentration is reduced from 18,752 ppm to 876 ppm.

COMPARATIVE EXPERIMENT 2

Not an Embodiment of the Invention

The two reaction zones described in Comparative Experiment 1 are utilized in the same manner except all the hydrogen flow is introduced to reaction zone 1 at the inlet, thus maintaining the same overall LHSV. The amount of hydrogen is varied in Comparative Experiments 2A and B, thus providing different $H_2$/BD ratios at the same LHSV; one $H_2$/BD ratio is lower and one $H_2$/BD ratio is higher than that of Comparative Experiment 1. Table 3 shows that this technique reduces 1-3-butadiene to no lower than 2657 ppm and results in a 42-50% loss of 1-butene and a large increase in n-butane.

TABLE 3

Results of C.E. 2; 1,3-butadiene removal from $C_4$ hydrocarbons using single inlet hydrogen addition.

| | 1-butene wt % | % 1-Butene loss | n-butane wt % | Cis + trans 2-butene wt % | 1,3 butadiene ppm | LHSV (hr−1) | Calculated wt % $H_2$ at bed inlet | $H_2$/BD molar in bed at inlet |
|---|---|---|---|---|---|---|---|---|
| Feed | 32.25 | | 4.22 | 54.31 | 18752 | | | |
| C.E. 2A All $H_2$ fed at inlet | 18.59 | 42.37 | 12.63 | 59.61 | 3228 | 1.33 | 0.037 | 0.53 |
| C.E. 2B All $H_2$ fed at inlet | 16.11 | 50.06 | 14.10 | 61.70 | 2657 | 1.33 | 0.456 | 6.6 |

TABLE 4

Mixed $C_4$ hydrocarbon feed stream composition for Example 3 and Comparative Experiment 4.

| | Wt % |
|---|---|
| Propane | 0.075 |
| Cyclopropane | 0.015 |
| Propylene | 0.038 |
| Isobutane | 0.323 |
| Butane | 4.24 |
| Cyclic C4 | 0.023 |
| t-2-Butene | 33.6 |
| 1-Butene | 28.3 |
| Isobutene | 5.58 |
| c-2-Butene | 25.3 |
| Isopentane | 0.098 |
| 1,3-Butadiene | 1.75 |
| Isopentene | 0.344 |
| Pentane Isomer-1 | 0.151 |
| Pentane Isomer-2 | 0.225 |

EXAMPLE 3

Four reaction zones in series are created containing 10 mL each of catalyst (about 5 g each) packed into ½" SS tubes. No external heating or cooling is applied to the reaction zones. The total $C_4$ hydrocarbon flow is 202 mL/hr providing an overall LHSV of 5 hr$^{-1}$. Each reaction zone is fed with 9 mL/min gaseous hydrogen, thus providing a hydrogen to 1,3-butadiene molar ratio as shown in Table 5. Zone outlet compositions are shown in Table 5.

The data in Table 5 show that the butadiene concentration is reduced from 17,533 ppm to 45 ppm, with a 1-butene loss of 23% and an increase in n-butane of 1.41 wt %.

COMPARATIVE EXPERIMENT 4

Not an Embodiment of the Invention

4A: The 4 reaction zones described in Example 3 are utilized in the same manner except that all the hydrogen flow is introduced to reaction zone 1 at the inlet (36 mL/min), thus maintaining the same overall LHSV and overall $H_2$/BD ratio as in Example 3. Table 6 shows that this technique reduces 1,3-butadiene to 550 ppm and results in a 42% loss of 1-butene and a 2.34 wt % increase in n-butane.

4B: C.E. 4A is repeated except that a larger catalyst volume is used (465 mL catalyst contained in a 500 mL SS vessel), thus reducing LHSV.

TABLE 5

4-zone 1,3-butadiene removal from $C_4$ hydrocarbon stream.

| | 1-butene wt % | % 1-Butene loss | n-butane wt % | Cis + trans 2-butene wt % | 1,3 butadiene ppm | LHSV (hr$^{-1}$) | Calculated wt % $H_2$ at bed inlet | $H_2$/BD molar in bed at inlet |
|---|---|---|---|---|---|---|---|---|
| Feed | 28.30 | | 4.24 | 58.84 | 17533 | 5 overall | 0.163 overall | 3.34 overall |
| Zone 1 outlet | 26.06 | 7.94 | 4.16 | 61.82 | 11212 | 20 | 0.041 | 0.63 |
| Zone 2 outlet | 26.13 | 7.67 | 4.27 | 62.29 | 4555 | 20 | 0.041 | 0.99 |
| Zone 3 outlet | 24.82 | 12.29 | 4.59 | 63.65 | 778 | 20 | 0.041 | 2.43 |
| Zone 4 outlet | 21.88 | 22.69 | 5.65 | 65.24 | 45 | 20 | 0.041 | 14.22 |

TABLE 6

Single reaction zone removal of 1,3-butadiene from $C_4$ hydrocarbon stream

| | 1-butene wt % | % 1-Butene loss | n-butane wt % | Cis + trans 2-butene wt % | 1,3 butadiene ppm | LHSV ($hr^{-1}$) | Calculated wt % $H_2$ at bed inlet | $H_2$/BD molar in bed at inlet |
|---|---|---|---|---|---|---|---|---|
| Feed | 28.30 | | 4.24 | 58.84 | 17533 | 5 overall | 0.163 overall | 3.34- overall |
| $H_2$ fed to zone 1 | | | | | | | | |
| Smaller volume single zone-example 4A | 16.50 | 41.69 | 6.58 | 69.95 | 550 | 5 | 0.163 | 3.34 |
| Bigger volume single zone-Example 4B | 18.72 | 33.86 | 8.38 | 66.07 | 440 | 0.43 | 0.163 | 3.34 |

The butadiene concentration in C.E. 4B is reduced from 17,533 ppm to 440 ppm using nearly an order of magnitude more catalyst while providing a longer residence time in the reaction zone for the olefin stream. Thus, this process is not as effective as the process of Example 3.

The preceding data demonstrate that the removal of 1,3-butadiene from a multi-component $C_4$ olefin stream by a staged addition of hydrogen into a plurality of reaction zones, rather than introducing the same amount of hydrogen via a single inlet at the beginning of one reaction zone, unexpectedly reduces 1,3-butadiene to lower levels while preserving more 1-butene in the process.

What is claimed is:

1. A process for hydrogenating a diolefin, the process comprising: contacting a liquid phase olefin stream containing from 200 ppm to 2 wt. % 1,3-butadiene, based on the total weight of the olefin stream, with a single catalyst and hydrogen in the substantial absence of carbon monoxide, wherein the contacting is conducted: (a) such that the hydrogen is fed into the process at at least 2 different hydrogen feed points, and the amount of hydrogen fed to at least one feed point is a substoichiometric amount, relative to the amount of the butadiene, and (b) under hydrogenation conditions sufficient to reduce the concentration of 1,3-butadiene to less than 100 ppm in at least one effluent stream of the process, wherein the feed rate of hydrogen is the same at the substoichiometric hydrogen feed point and at least one additional hydrogen feed point.

2. The process of claim 1 wherein the olefin comprises 1-butene.

3. The process of claim 1, wherein the $H_2$ is essentially fully dissolved in the liquid phase.

4. The process of claim 1, wherein the conversion of 1,3-butadiene at the $2^{nd}$ hydrogen feed point is at least 20%.

5. The process of claim 1, wherein the process has at least 3 hydrogen feed points.

6. The process of claim 1, wherein the process has at least 4 hydrogen feed points.

7. The process of claim 1, wherein the conversion of 1,3-butadiene at the $2^{nd}$ hydrogen feed point is at least 40%.

8. The process of claim 1, wherein the hydrogenation conditions are sufficient to reduce the concentration of 1,3-butadiene to less than 50 ppm.

9. The process of claim 1, wherein the contacting is conducted in more than one reactor.

10. The process of claim 1, wherein the contacting is conducted in a single reactor.

11. The process of claim 1, wherein the effluent stream is sent to a hydroformylation process.

12. The process of claim 1, wherein the contacting of the liquid phase olefin stream with the single catalyst and hydrogen is in the absence of carbon monoxide.

13. The process of claim 1, wherein the amount of hydrogen fed to at least two feed points is a substoichiometric amount, relative to the amount of the butadiene.

* * * * *